United States Patent [19]

Hai et al.

[11] Patent Number: 5,128,452
[45] Date of Patent: Jul. 7, 1992

[54] PROCESS FOR THE PRODUCTION OF CROSSLINKED HEMOGLOBIN IN THE PRESENCE OF SODIUM TRIPOLYPHOSPHATE

[75] Inventors: Ton T. Hai, Lake Villa; Deanna J. Nelson, Libertyville; Ana Srnak, Skokie, all of Ill.

[73] Assignee: Baxter International Inc., Deerfield, Ill.

[21] Appl. No.: 340,609

[22] Filed: Apr. 19, 1989

[51] Int. Cl.$^5$ .................. A61K 35/14; C07K 3/08; C07K 13/00
[52] U.S. Cl. .................................................. 530/385
[58] Field of Search ........................... 514/6; 530/385

[56] References Cited

U.S. PATENT DOCUMENTS 4,598,064 7/1986 Walder .......................... 530/385
4,600,531 7/1986 Walder .......................... 530/385

OTHER PUBLICATIONS

Chanutin et al., (1967), Effect of Organic and Inorganic Phosphates on the Oxygen Equilibrium of Human Erythrocytes, Arch. Biochem. Biophys., 121:96–102.
Chanutin et al., (1969), Interaction of Organic and Inorganic Phosphates with Hemoglobin., Arch. Biochem. Biophys., 131:180–184.

Primary Examiner—Robert A. Wax
Assistant Examiner—Richard C. Ekstrom
Attorney, Agent, or Firm—Paul C. Flattery; Sarah E. Bates

[57] ABSTRACT

A process for the production of crosslinked hemoglobin comprises crosslinking hemoglobin in the presence of sodium tripolyphosphate.

9 Claims, No Drawings

PROCESS FOR THE PRODUCTION OF CROSSLINKED HEMOGLOBIN IN THE PRESENCE OF SODIUM TRIPOLYPHOSPHATE

This invention was made with government support under Contract DAMD17-85-C-5194 awarded by the Department of the Army. The Government has certain rights in this invention.

FIELD OF THE INVENTION

The present invention relates to a process for the production of crosslinked hemoglobin, useful as a blood substitute and plasma expander.

BACKGROUND OF THE INVENTION

There is a great need in the medical industry for blood substitutes and plasma volume expanders. Blood substitutes are useful for replacing blood lost by acute hemorrhage or during surgery, for supplying oxygen to tissues and organs and generally maintaining blood volumes. Plasma expanders are useful in volume deficiency shock, as an alleviant in anaphylactic and allergic shock and for replacing plasma lost following burn injuries. Donor blood banks have proved to be inadequate to meet this need for a number of reasons. Not only do blood banks often experience a shortage of donor blood, but blood that is donated can be unacceptable for medical use. Donor blood can be contaminated with hepatitis or the acquired immune deficiency syndrome (AIDS) virus, thereby posing significant risks to patients who receive the blood. In addition, donated blood has a relatively short shelf life.

In view of these problems, there has been extensive interest in the development of blood substitutes and blood plasma expanders which can be easily prepared and used in place of donated blood. To be effective, such a substitute should be characterized by a sufficiently high oxygen-binding capacity for use under normal environmental conditions. It also should not be subject to rapid renal elimination.

One type of substitute that has generated significant interest is modified hemoglobins. Natural mammalian hemoglobin is a tetramer, i.e., it is characterized by four polypeptide chains, two identical alpha chains and two identical beta chains, that are noncovalently linked together. In plasma, oxygenated hemoglobin has a tendency to split into dimers, each of which is small enough to be filtered by the kidneys and be excreted. Such dimers thus potentially cause renal damage and have significantly decreased intravascular retention time. As a result of the shortcomings of natural hemoglobin, efforts have been made to modify the hemoglobin molecule to make it resistant to dimerization.

Known treatments for crosslinking hemoglobin to make it resistant to dimerization involve reaction of hemoglobin with bifunctional reagents such as glutaraldehyde (C. Hopwood et al., *Histochem J.* 2, 137, 1970), glycolaldehyde (J. M. Manning, "Carboxymethylated Cross-Linked Hemoglobin A as a potential Blood Substitute", Abstract in the *Program and Abstracts, Symposium on Oxygen Binding Heme Proteins Structure, Dynamics, Function and Genetics*, Asilomar Conference Grounds, Pacific Grove, Calif., Oct. 9-13, 1988) or diimidate esters (W. Mock et al., Fed. Proc. 34, 1458, 1975, and U.S. Pat. No. 3,925,344). In U.S. Pat. No. 4,473,496, linear alpha-omega or heterocyclic polyaldehydes containing negatively charged groups are described as suitable for both decreasing the oxygen affinity of hemoglobin and for producing inter- and intramolecular crosslinking of hemoglobin. These reagents include carbohydrate-containing molecules such as mono- and polyphosphorylated nucleotides partially oxidized with periodate, so as to obtain aldehydic groups. The coupling reaction is based on the formation of Schiff bases of the aldehydic groups with the amino groups of the hemoglobin molecule. The schiff bases are then transformed into stable, covalent bonds by reduction with sodium or potassium borohydride, or another strong reducing agent. Finally, U.S. Pat. No. 4,584,130 describes the use of bifunctional crosslinking reagents such as diethyl 2,2'-sulfonyl-bis-malonate, ethyl 2,2'-sulfonyl-2,2'-benzenesulfonyl-bis-acetate, and the like, that have utility in crosslinking stroma-free hemoglobin to provide a modified hemoglobin having a physiologically acceptable oxygen affinity and suitable circulating half-life in vivo.

Another modified hemoglobin is described in U.S. Pat. No. 4,598,064 to Walder (1986). Specifically, Walder teaches crosslinking the two alpha chains of the tetrameric hemoglobin molecule, specifically at Lys 99 Alpha$_1$ and Lys 99 Alpha$_2$. A second patent by Walder, U.S. Pat. No. 4,600,531 (1986), discloses what the patentee describes as a process for the high level production of alpha, alpha-crosslinked hemoglobin. In accordance with this process, unmodified hemoglobin is deoxygenated and crosslinked, with the crosslinking occurring in the presence of an added polyanion which binds electrostatically to deoxyhemoglobin at the 2,3-diphosphoglycerate binding site, located between the beta chains. This blocks side reactions of the crosslinker within this site and neighboring regions of the protein, thereby enhancing the chances of reaction at the desired Lys 99 Alpha$_1$ and Lys 99 Alpha$_2$ site, access to which is not blocked by the polyanion. Suitable polyanions are said to be 2,3-diphosphoglycerate, inositol hexaphosphate (IHP) and inositol hexasulfate, with IHP said to be preferred. The patent states that the concentration of polyanion should be within the range of from equimolar amounts with the hemoglobin to as much as a twenty molar excess, preferably from about 5 times to about 10 times the molar amount of hemoglobin.

In the examples section of the patent, Walder shows that, when bis(3,5-dibromosalicyl) fumarate was used as crosslinking agent in the absence of IHP, the yield of the desired crosslinked product was only about 5%. Approximately 10-15% of the hemoglobin was unmodified at the conclusion of the reaction period. Side reactions at other sites on the protein accounted for the remaining material. In the presence of 1.5 mM, however, as shown in example 3, the yield of alpha, alpha-crosslinked hemoglobin was found to be increased to 40%. At 5 mM IHP, the yield of alpha, alpha-crosslinked derivative was 60-65% with less than 6% impurities due to side reactions at other sites of the protein. Walder states that there were no further improvement in yield if the concentration of IHP was further increased.

Similarly, in example 5 of the Walder patent, under similar reaction conditions, at IHP concentrations of 1.3 and 1.5 mM, the yield was between 55% and 65%. At IHP concentrations of 2.0 mM or more, the yield of desired product was found to decrease progressively because of side reactions at other sites on the protein.

In addition to the limitations on product yield, the process described by Walder, although useful, has been found to have a number of other disadvantages. First, the use of IHP causes significant increases in the percentages of methemoglobins in the product mixture. These methemoglobins are not useful as blood substitutes of plasma expanders, nor do they have any other known clinical applications. The amount of methemoglobin formed can be decreased if the crosslinking reaction is carried out at temperatures of 25° C. or lower. This has proved to be impractical, however, for it has been found that if the reaction is carried out at less than about 37° C., the yield of the desired alpha, alpha-crosslinked protein is reduced, even when extended reaction times are used.

It also has been found that if the IHP is not removed from the product mixture after crosslinking is complete and prior to subsequent manipulations of the product mixture, oxidation of the various modified and unmodified hemoglobins to methemoglobins is accelerated relative to rates of methemoglobin formation in the absence of IHP. It is possible to remove the IHP from the reaction mixture once the crosslinking reaction has gone to completion but prior to subsequent manipulations of the product mixture. This procedure, however, adds a step, and, therefore, time and expense to the reaction process described by Walder. The additional step also increases the opportunity for chance microbial or pyrogen contamination of the product.

Yet another disadvantage of the Walder process is that, if the crosslinking reaction is completed using crude hemoglobin lysates, the yield of alpha, alpha-crosslinked hemoglobin is consistently less than the yield that is realized when purified hemoglobin lysates are used. When operating on a commercial scale, however, the use of crude hemoglobin lysates is preferred for hemoglobin modification processes.

Accordingly, improvements of the process disclosed by Walder are sought. It is an object of the present invention to provide a process for the formation of crosslinked hemoglobin in which the yields of desired product are enhanced in comparison to the yields obtainable using the prior art processes. It is a further object of this invention to develop such as process in which the levels of methemoglobins produced are relatively low.

Further objects of this invention will be apparent from reading the description of the invention set forth below and the appended claims.

SUMMARY OF THE INVENTION

In accordance with the present invention, there is disclosed an improved process for making crosslinked hemoglobin. The process comprises adding sodium tripolyphosphate (STP) to a hemoglobin solution and crosslinking the hemoglobin in solution.

DETAILED DESCRIPTION OF THE INVENTION

The present invention provides an improved process for making crosslinked hemoglobin. A solution of sodium tripolyphosphate is added to a hemoglobin solution. The hemoglobin is then crosslinked. The process increases the yields of crosslinked hemoglobin over those obtained by processes known in the art. In addition, the process of the present invention reduces the conversion of hemoglobins to methemoglobins in comparison with conversion levels which occur in the processes of the prior art.

The hemoglobin starting material can be obtained from a number of sources. For example, from human blood cells hemoglobin can be obtained from freshly drawn blood or from blood samples which are to be discarded because they have exceeded the limits of safe shelf life. Alternatively, the hemoglobin may be obtained from other mammalian cells or produced by recombinant DNA techniques. The hemoglobin solution can be purified by a variety of techniques known in the literature such as filtration, chromatography, centrifugation, or precipitation. Hemoglobin is preferably prepared by a process of washing, lysing and filtering red blood cells. However, such purification is not essential to the invention.

Sodium tripolyphosphate (STP) is then added to the hemoglobin. Preferably a solution of STP is added to the hemoglobin solution. Applicants believe that the STP acts to maintain hemoglobin in a low oxygen affinity conformation. It also acts as a blocking agent to prevent crosslinking between the beta chains in the subsequent hemoglobin crosslinking reaction. The STP solution has a pH in the range of about 5.0 to about 10.5, preferably about 5.8. The pH can be adjusted to bring it within the desired range by the addition of an acid, such as acetic acid or hydrochloric acid. Following addition of the STP solution to the hemoglobin, small amounts of a base can be added to bring the pH of the resulting solution to within the range of about 6.5 to about 7.5, preferably about 6.9.

Preferably, the hemoglobin in the solution is then deoxygenated. The hemoglobin can be deoxygenated by any one of several procedures. For example, the hemoglobin-containing solution can be circulated through a membrane charged with an inert gas, such as nitrogen, carbon dioxide or argon, prior to crosslinking. Alternatively, hemoglobin can be deoxygenated by reacting it with sodium dithionite or other known reducing agent such as sodium metabisulfite.

Also, exposure to a vacuum may be used to deoxygenate. When the hemoglobin is deoxygenated in the presence of STP, the rate of formation of methemoglobin does not increase.

Following deoxygenation, the hemoglobin is crosslinked. As reported in Walder in U.S. Pat. No. 4,600,531, one general class of suitable crosslinkers is diaspirin derivatives of dicarboxylic acids. Certain dialdehydes, alkyl halides, sulfonate esters or other alkylating agents also can be used to crosslink. The preferred crosslinking agent is bis(3,5-dibromosalicyl) fumarate (DBBF).

It surprisingly has been determined that when the DBBF-crosslinking reaction is carried out in the presence of STP, the yields of the desired crosslinked hemoglobin are increased in comparison of the yields obtained using the procedures of the prior art. In a preferred embodiment, the crosslinking reaction is carried out by adding a solution of the crosslinking agent, bis(3,5-dibromosalicyl) fumarate, to the solution of STP and deoxygenated hemoglobin. Desirably, the solution of the crosslinking agent has been saturated with an inert gas, such as nitrogen, prior to its addition to the other reactant solution. The molar ratio of DBBF to deoxygenated hemoglobin desirably ranges from about 1.2:1 to about 2.5:1 and preferably is about 1.8:1. The pH of the reaction can vary from about 6.5 to about 7.5 and preferably is from about 6.8 to about 7.0.

The crosslinking reaction is carried out at a temperature of about 5° C. to about 40° C.; for DBBF the temperature is preferably 37° C. The progress of the reaction can be monitored by gel permeation high pressure liquid chromatography. When a desired degree of crosslinking has occurred, the reaction can be terminated; for DBBF this can be accomplished through the addition of a nitrogen-saturated glycine solution, or by cooling. Known methods such as filtration, precipitation, or chromatography may be used to separate and purify the crosslinked hemoglobin from the reaction.

As discussed above, when IHP is used in the crosslinking reaction, it is desirable to remove the IHP from the product solution as quickly as possible following completion of the reaction in order to avoid conversion of the hemoglobins to methemoglobins. One advantage of the present process is that prompt removal of the STP from the product solution is not necessary.

Crosslinked hemoglobin formed in accordance with the procedures of the present invention generally is found to comprise at least 90% of the total hemoglobin product produced. Methemoglobin generally is found to constitute about 5% of the total product or less. Other modified hemoglobins make up the remained of the final product.

The crosslinked hemoglobin has been found capable of transporting and supplying oxygen to tissues and organs and to maintain oncotic pressure. It also is characterized by a resistance to dimerization and rapid removal from circulation by renal elimination. Accordingly, it can be used as an effective blood substitute or plasma expander. The crosslinked hemoglobin can be used as is, mixed with as known pharmaceutically acceptable carrier, or mixed with other known blood substitutes and plasma expanders.

The following example is provided to further illustrate the present invention but are not be construed as limiting.

EXAMPLE

Approximately 6 liters of human red blood cells that were obtained from units of blood that had exceeded the approved storage period were used to prepare stroma free hemoglobin lysate.

1572 ml. (110 g., 1.705 mmol., pH 5.95) of hemoglobin lysate were transferred to a fermentor. 9.4 grams of sodium tripolyphosphate (STP) were added to 100 ml. of water and the pH was adjusted to 5.8 by the addition of 32.5 ml. of 1M acetic acid. The STP solution was added to the hemoglobin lysate and the pH was adjusted to 6.9 through the addition of 33 ml. of 0.3M KOH. 100 ml. of water were added to adjust the hemoglobin concentration to 6.0 g/dl. The solution was exposed to nitrogen to deoxygenate the hemoglobin at ambient temperature.

Following deoxygenation, the reaction temperature was raised to 37° C. 50 ml. of a nitrogen-saturated solution of bis(3,5-dibromosalicyl) fumarate (DBBF) (2.293 g., 1.9 equiv.) in 1M HEPES, pH 7.25, were added to the hemoglobin-STP solution. The solution was stirred under nitrogen and progress of the crosslinking reaction was monitored by gel permeation high pressure liquid chromatography. After 4.5 hours the reaction was terminated by cooling to 5° C. The pH of the product solution was increased to 7.5 by the addition of 53 ml. of nitrogen-saturated 0.3M KOH. The solution then was purified by filtration, heat treatment and diafiltration.

The final product was obtained in 74% overall yield, based on initial hemoglobin used. The product was determined by reversed-phase pressure liquid chromatography to contain more than 95% crosslinked hemoglobin. Ultraviolet-visible spectrophotometric analysis indicated that the product contained 4.8% methemoglobin.

Although the invention is described in detail with reference to specific embodiments thereof, it will be understood that variations can be made without departing from the scope of the invention as described above and as claimed below.

We claim:

1. A process for making crosslinked hemoglobin comprising: adding sodium tripolyphosphate to a hemoglobin solution and reacting the hemoglobin with a crosslinking agent.

2. A process for making crosslinked hemoglobin comprising: lysing red blood cells to produce a hemoglobin containing lysate, adding sodium tripolyphosphate to the lysate, deoxygenating the hemoglobin in the lysate, and reacting the hemoglobin with a crosslinking agent.

3. The process of claim 1 wherein the crosslinking agent is a member selected from the group consisting of glutaraldehyde, glyoxylate, polyether glycols, bis(3,5-dibromosalicyl) diesters and bis(3,5-dibromosalicyl) fumarate.

4. The process of claim 2 wherein the crosslinking agent is a member selected from the group consisting of glutaraldehyde, glyoxylate, polyether glycols, bis(3,5-dibromosalicyl) diesters and bis(3,5-dibromosalicyl) fumarate.

5. The process of claim 1 wherein the molar ratio of hemoglobin to sodium tripolyphosphate is from about 1:1 to about 1.30.

6. The process of claim 2 wherein the molar ratio of hemoglobin to sodium tripolyphosphate is from about 1:1 to about 1.30.

7. The process of claim 3 wherein the molar ratio of hemoglobin to crosslinking agent is from about 1:1 to about 1:50.

8. The process of claim 3 wherein the crosslinking reaction is conducted to a temperature of about 5° C. to about 40° C.

9. The process of claim 2 wherein the pH of the hemoglobin and sodium tripolyphosphate solution is within the range of 6.5 to about 10.0 prior to deoxygenating the hemoglobin.

* * * * *